US008118918B2

(12) United States Patent
Knox et al.

(10) Patent No.: US 8,118,918 B2
(45) Date of Patent: Feb. 21, 2012

(54) IN-LINE SMOKE ATTENUATOR

(75) Inventors: Ron Knox, Mount Eliza (AU); Scott James Martin, Richmond (AU); Scott Anthony Wilson, Donvale (AU); Megan Wilson, legal representative, Donvale (AU)

(73) Assignee: Xtralis Technologies Ltd., Nassau (BS)

( * ) Notice: Subject to any disclaimer, the term of this patent is extended or adjusted under 35 U.S.C. 154(b) by 638 days.

(21) Appl. No.: 12/224,190

(22) PCT Filed: Feb. 20, 2007

(86) PCT No.: PCT/AU2007/000189
§ 371 (c)(1),
(2), (4) Date: Aug. 20, 2008

(87) PCT Pub. No.: WO2007/095675
PCT Pub. Date: Aug. 30, 2007

(65) Prior Publication Data
US 2009/0002182 A1    Jan. 1, 2009

(30) Foreign Application Priority Data
Feb. 20, 2006   (AU) .............................. 2006900823

(51) Int. Cl.
*B01D 50/00* (2006.01)
(52) U.S. Cl. ................ 95/273; 96/413; 96/422; 55/418; 73/863.23; 73/863.41
(58) Field of Classification Search ............. 55/337, 55/413, 418, 458, 459.1, 462, 463, 331, 349, 55/459.2, 459.5, 457, 476, 321, 410; 422/176, 422/169; 60/298, 299, 324; 73/863.23, 863.41; 95/273, 23; 96/413, 422

See application file for complete search history.

(56) References Cited

U.S. PATENT DOCUMENTS

| | | | |
|---|---|---|---|
| 3,976,450 A * | 8/1976 | Marcote et al. ................... | 96/12 |
| 5,058,440 A | 10/1991 | Graze, Jr. | |
| 5,163,986 A * | 11/1992 | Bielefeldt ........................ | 55/346 |
| 5,332,512 A | 7/1994 | Wells | |

(Continued)

FOREIGN PATENT DOCUMENTS

DE          10110156          9/2002

OTHER PUBLICATIONS

"International Application Serial No. PCT/AU2007/000189, International Search Report mailed May 23, 2007", 4 pgs.

(Continued)

*Primary Examiner* — Duane Smith
*Assistant Examiner* — Minh-Chau Pham
(74) *Attorney, Agent, or Firm* — Schwegman, Lundberg & Woessner, P.A.

(57) ABSTRACT

In one form the present invention provides an apparatus in an airflow path before a particle detector, wherein the apparatus removes a substantially constant proportion of all sizes of airborne particles from the airflow over time. In an example the apparatus includes a flow splitting arrangement configured to divide a fluid flow into a plurality of sub-flows, the splitting arrangement 10 including means for defining a plurality of substantially identically dimensioned flow apertures configured to direct a portion of the fluid into a respective sub-flow.

16 Claims, 4 Drawing Sheets

U.S. PATENT DOCUMENTS

| | | | |
|---|---|---|---|
| 5,484,575 A * | 1/1996 | Steenackers | 422/176 |
| 6,090,175 A * | 7/2000 | Richard | 55/337 |
| 6,712,869 B2 * | 3/2004 | Cheng et al. | 55/418 |
| 7,097,682 B2 * | 8/2006 | Tanaka et al. | 55/385.4 |
| 7,637,972 B2 * | 12/2009 | Bergami | 55/321 |
| 2004/0065200 A1 * | 4/2004 | Lo et al. | 95/269 |
| 2004/0226273 A1 * | 11/2004 | Lorey et al. | 55/385.2 |

OTHER PUBLICATIONS

"International Application Serial No. PCT/AU2007/000189, Written Opinion mailed May 23, 2007", 7 pgs.

* cited by examiner

IN-LINE SMOKE ATTENUATOR

RELATED APPLICATIONS

This application is a nationalization under 35 U.S.C. 371 of PCT/AU2007/000189, filed Feb. 20, 2007 and published as WO 2007/095675 A1 on Aug. 30, 2007, which claimed priority under 35 U.S.C. 119 to Australian Patent Application Serial No. 2006900823, filed Feb. 20, 2006; which applications and publication are incorporated herein by reference and made a part hereof.

FIELD OF INVENTION

The present invention relates to an improved method and apparatus for particle detection. In a preferred form, the present invention relates to a method and apparatus for filtering an air sample before applying it to a particle detector.

It will be convenient to describe the invention as applied to smoke detection, however the invention should not be construed as being limited to this exemplary field of use.

BACKGROUND OF THE INVENTION

Particle detectors are often used to warn of the presence of smoke emanating from a potential or incipient fire. Particle detectors of the scattering light type operate by exposing an air sample, that is drawn from an area being monitored, to light, and detecting light scattered from any particles in the air. Air, for example from a factory or office, usually contains some level of particles, and the detector can be set to alarm at certain levels which are higher than background particle levels, and are believed to be indicative of smoke.

The environments that scattering type smoke detectors operate in vary widely, and include, for example, office environments, factories and manufacturing plant, power stations and clean rooms. Each of which has different levels of background particulate material.

A problem can be encountered with such smoke detection apparatus if they are continuously exposed to the relatively high levels of background pollution in the air that can exist in some environments. A large-scale example in recent years has been the high levels of smoke pollution often present in widespread regions of Asia, which have a high dependency on the burning of brown coal.

Background smoke pollution can cause soiling of components of the detector leading to premature failure, for example due to clogging of air paths or changes in the optical properties of the detection chamber itself.

Attempts to overcome this problem have included dust filters placed in the airstream. Dust filters have been used to filter out particles not associated with the smoke to be detected. Smoke particles may occur in a variety of sizes depending on the fuel used and combustion conditions, and the filter type is chosen according to type of dust particles expected and the type of smoke to be detected.

However, as conventional dust filters clog they begin to remove more particles from the air and will eventually begin filtering out smoke particles (or other small particles of interest). This may be due to effective pore size of the filter being reduced as more particles clog the filter. This can be a problem because such filters start undesirably removing smoke particles before the flow rate changes appreciably. The result is that the filter may be removing an unknown proportion of smoke, but this is not detectable using flow-meters.

In some situations attempts have been made to condition the air sample prior to its introduction into the smoke detector e.g. by diluting the sample flow with clean air. The object of such dilution is to arrive at a sample flow with an unchanged particle distribution, but with a lower particle concentration than the original sample flow.

Dilution can be used to effectively reduce the concentration of particulate material reaching the detector, but presents problems for air sampling smoke detectors that use a pipe network to draw air from a space being monitored, in that the introduction of the diluent air flow into the flow entering the detector reduces the amount of sample air drawn from the region being monitored. This causes an increase in the time taken for the sample air to travel from the region being monitored to the smoke detector, and consequently increases detection time.

One proposed dilution filter, described in U.S. Pat. No. 5,332,512 to Wells splits the sample flow into two sub-flows, and filters one of the flows to remove all particles from it. The filtered and unfiltered sample flows are then recombined.

The present inventors have ascertained that such a device would address the transport time increase identified above without requiring a substantial increase in aspirator power, however, the dilution ratio of such a device would change over time making taking reliable particle measurement difficult. More importantly the inventors have identified that the dilution ratio will increase as the capillary, through which the unfiltered air passes, clogs. Ultimately this may lead to no particles passing through the filter arrangement, which is undesirable.

SUMMARY OF THE INVENTION

In a first aspect there is provided an apparatus in an airflow path before a particle detector, wherein the apparatus removes a substantially constant proportion of all sizes of airborne particles from the airflow over time.

The apparatus may further include a flow splitting arrangement for dividing the airflow into at least a first sub-flow and a second sub-flow, and a filtering arrangement for filtering the first sub-flow.

In some embodiments the filter arrangement preferably removes substantially all particulate matter from the first sub-flow.

The filtering arrangement can include a HEPA filter and/or an electrostatic filtering means.

The flow splitting arrangement preferably includes a plurality of apertures through which the airflow passes to divide it into sub-flows.

The plurality of apertures formed in the flow splitting arrangement are preferably substantially identical to each other.

In certain embodiments the relative proportion of the airflow split into each sub-flow corresponds to the proportion of the apertures formed in the flow splitting arrangement configured to direct the airflow into each sub-flow.

Preferably the flow spitting device has an impedance to the passage of the sub-flows that is substantially greater than the flow impedance caused by the filtering arrangement. In certain embodiments, in the event that the filtering arrangement is clogged so that it removes particles to be detected by the particle detector to by unacceptable extent, the flow impedance of the flow splitting arrangement flow is substantially greater than the flow impedance caused by the filtering arrangement.

In some embodiments the apparatus further includes, at least one flow meter for determining a flow rate in any of the following:
an inlet to the apparatus;

an outlet from the apparatus;
a flow path through which one or more of the sub-flows passes.

The apparatus may include a plurality of flow meters.

In a second aspect the present invention provides a method of filtering an air sample prior to introduction to a particle detection means, the method including: dividing the air sample into at least two sample flows; filtering one or more of the sample flows; restricting the flow of the sample flows by an amount greater than a flow restriction caused by the filtering of the one or more sample flows; and re-combining at least some of the sample flows prior to introduction to a particle detection means.

Preferably at least one sample flow is not filtered before being re-combined with another sample flow.

The step of restricting the one or more filtered sample flows can be performed either before or after the filtering of the sample flow.

The method can further include measuring any one or more of;
a flow of filtered air;
a flow of unfiltered air;
a sample flow;
the flow of air prior to dividing it into sample flows; and
the flow of air after combining sample flows compared to a total flow.

In a third aspect there is provided an apparatus for a smoke detector including a first flow path having a filter and an aspirator, a second flow path having an aspirator, and a controller, such that the aspirators adjust the flow in the first and second flow paths to provide a predetermined ratio of filtered to unfiltered air.

In another aspect there is provided an arrangement for conditioning a fluid flow, the arrangement including:
a first flow path;
a second flow path,
a filter arrangement to filter the fluid flow in the first flow path; and
a flow splitting arrangement for splitting the fluid flow into either the first flow path or the second flow path,
wherein the impedance to the fluid flow caused by the flow splitting arrangement is greater than the impedance caused to the fluid flow by the filter.

In yet another aspect the present invention provides an arrangement for conditioning a fluid flow including:
a chamber including a fluid inlet and a fluid outlet;
an unfiltered fluid flow path extending between the fluid inlet and the fluid outlet;
a filtered fluid flow path extending between the fluid inlet and the fluid outlet;
a filtering means for filtering the fluid flowing through the filtered fluid flow path;
a flow splitting arrangement for splitting the fluid flow into the filtered fluid flow path or the unfiltered fluid flow path,
wherein the impedance to the fluid flow caused by the flow splitting arrangement is greater than that caused by the filtering means.

The flow splitting arrangement can include at least one first aperture leading to the filtered fluid flow path and at least one second aperture leading to the unfiltered fluid flow path, and wherein the flow impedance caused by each first and second aperture is substantially the same. Preferably, the proportion of the fluid flow split into the filtered fluid flow path and unfiltered fluid flow path respectively is determined by the relative number of first and second apertures.

In a further aspect, the present invention provides a flow splitting arrangement configured to divide a fluid flow into a plurality of sub-flows, the splitting arrangement including means for defining a plurality of substantially identically dimensioned flow apertures configured to direct a portion of the fluid into a respective sub-flow, wherein the relative proportion of the fluid flow that is split into each sub-flow is determined by the relative proportion of the identically dimensioned flow apertures configured to direct a portion of the air into each respective sub-flow.

Preferably, the flow means for defining a plurality of substantially identically dimensioned flow apertures is a body having a plurality of substantially identical apertures formed therein.

The body can be a plate-like member having a plurality of holes of equal diameter extending through it to define said flow apertures.

In another aspect, the present invention provides a method of detecting particles in an air sample, including:
(a) obtaining an air sample;
(b) reducing the concentration of particles in the air sample;
(c) detecting a level of particles in the air sample with reduced particle concentration;
(d) applying a correction to the detected level of particles corresponding to the reduction in concentration of particles in the air sample produced in step (b).

Step (b) may further include, splitting the air sample into sub flows;
filtering less than all of the sub-flows; and re-combining at least one filtered and one unfiltered sub-flow to generate an air sample with a reduced concentration of particles.

In another aspect the present invention provides an apparatus for a smoke detector including a first flow path having a filter and an aspirator, a second flow path having an aspirator, and a controller, such that the aspirators adjust the flow in the first and second flow paths to provide a predetermined ratio of filter to unfiltered air.

Embodiments of this aspect of the invention have the advantage that the ratio of filtered air to unfiltered air can be adjusted or kept constant when the impedance of the filtered flow path changes.

BRIEF DESCRIPTION OF THE DRAWINGS

An illustrative example configuration for such a device is described, by way of non-limiting example only, with reference to the accompanying drawings in which.

DETAILED DESCRIPTION OF THE PREFERRED EMBODIMENTS

Figure 1:
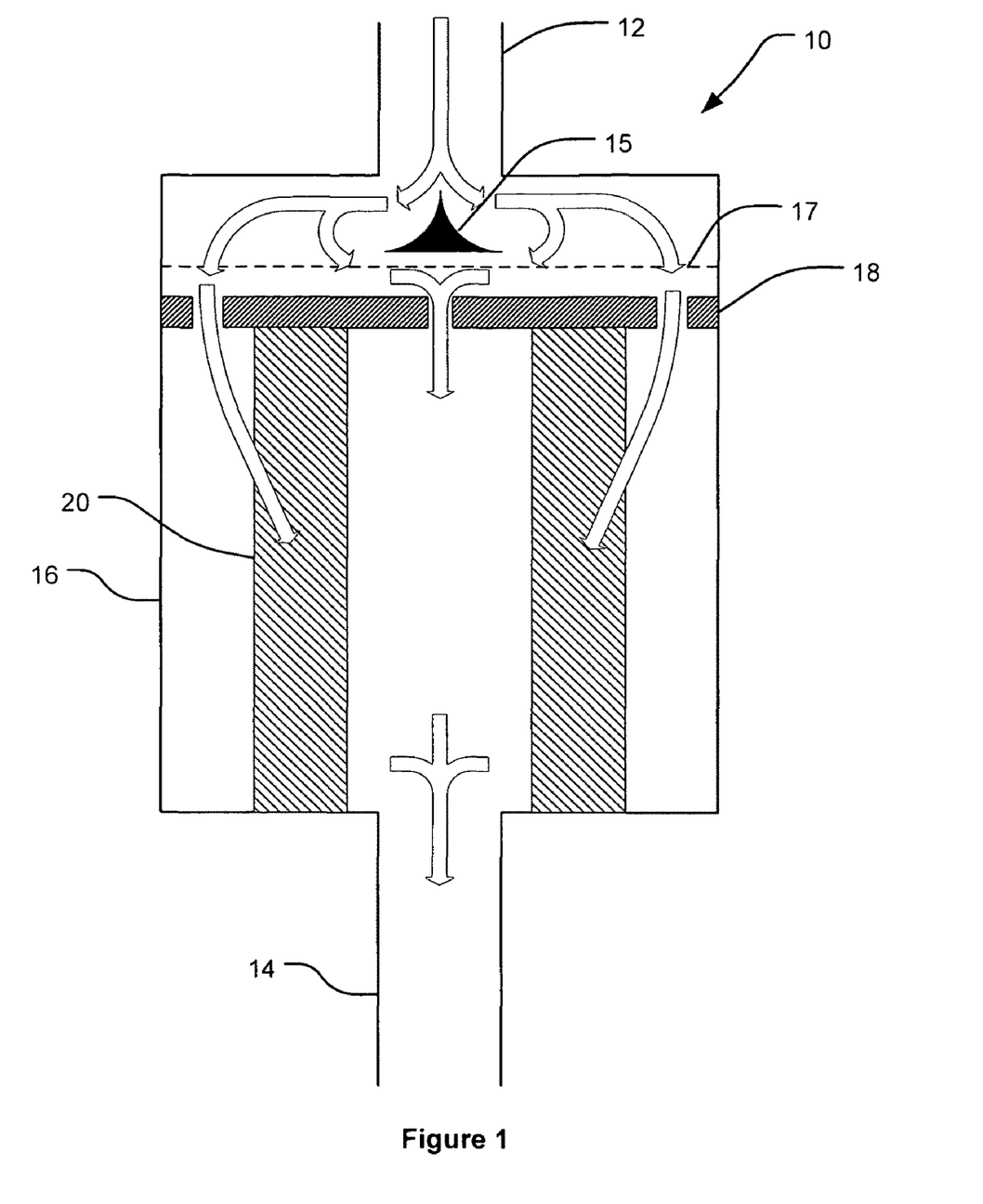
FIG. 1 is a schematic cross section of an example of a smoke attenuator.

In FIG. 1 filtering apparatus 10, hereinafter termed a "smoke attenuator" is shown, having an inlet 12, an outlet 14, and a housing 16. Within the housing 16 is a flow separator 18 (shown in FIG. 2) and a filter 20 (shown in FIGS. 1, 2 and 3). In the present example the flow separator 18 is a plate 21 having a number of apertures 22 and 23 formed in it. These apertures are shown in greater detail in FIG. 2. In this example the flow separator separates the single flow of air entering the inlet into a filtered sub-flow (air passing through apertures 22) and an unfiltered sub-flow (air passing through aperture 23). The filtered and un-filtered sub-flows recombine in the area after the filter, before exiting the filter outlet 14. A flow distributor may be placed near the inlet 12 to assist in distributing the flow evenly within the housing. An insect screen 17, e.g. formed from a wire mesh, may also be placed within the housing to prevent insects and very large particulate material from contaminating the filter 20, or from passing via the un-filtered flow path into downstream components, such as a particle detector.

In alternative embodiments the sub-flows can remain separate for as long as desired so long as they are re-combined before entry into the particle detection means.

In the present example, the smoke attenuator is designed to reduce smoke concentration by a factor of 10. To achieve such a result, one tenth of the airflow is separated into a sub-flow by being directed through an aperture that introduces the sub-flow into a flow path that bypasses the filter, and nine tenths are directed through apertures that require the airflow to pass through a filter before exiting the housing. In the particular example shown in FIGS. 1 to 4, the filter is a high efficiency low impedance filter, such as a HEPA filter. In an alternative embodiment, the filter could be an electrostatic filter.

Figure 2:
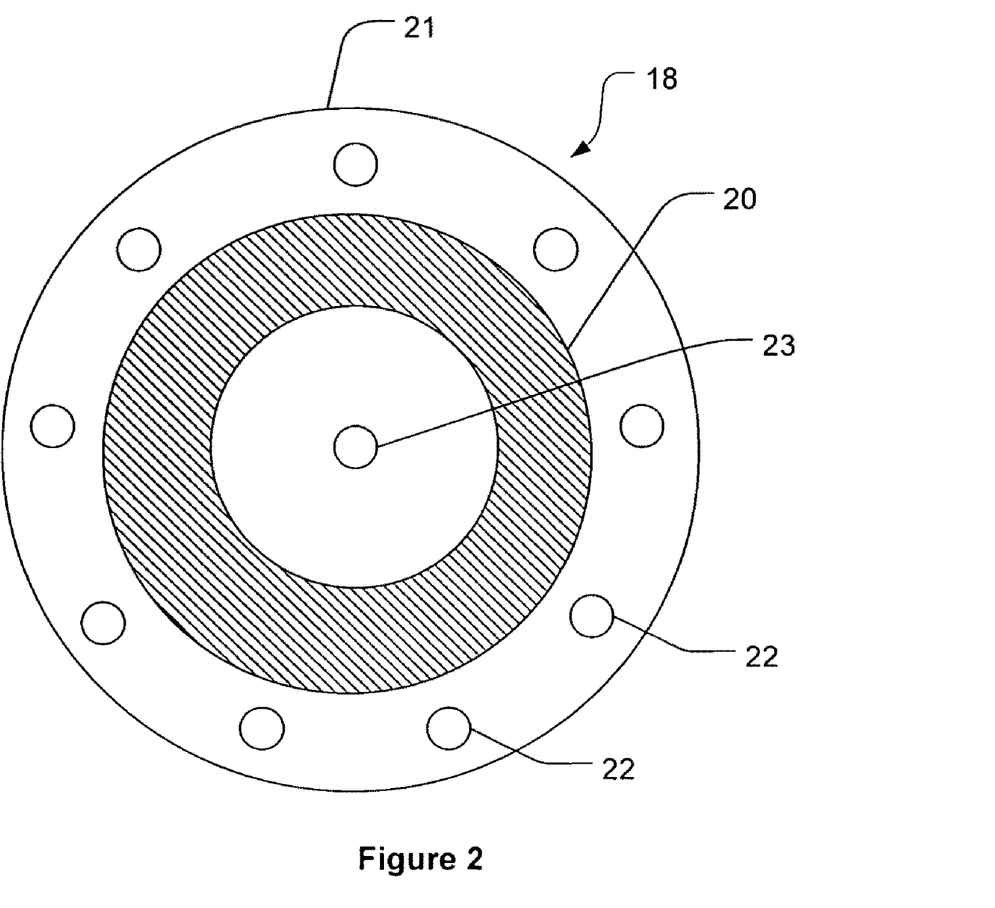
FIG. 2 is a schematic top view of a perforated plate of the smoke attenuator of FIG. 1.
Figure 3:
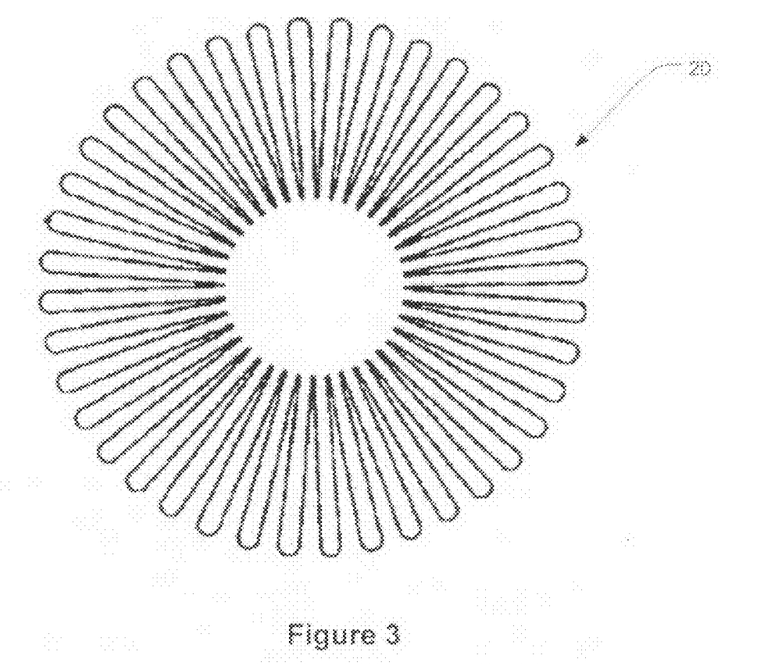
FIG. 3 is a schematic cross section of a filter of the smoke attenuator of FIG. 1.
Figure 4:
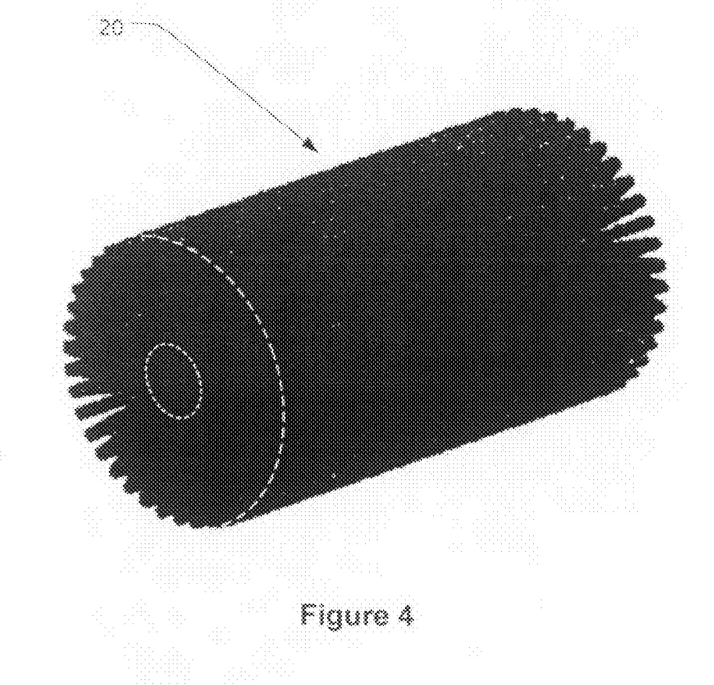
FIG. 4 is a perspective view of the filter of FIG. 3.
Figure 5:
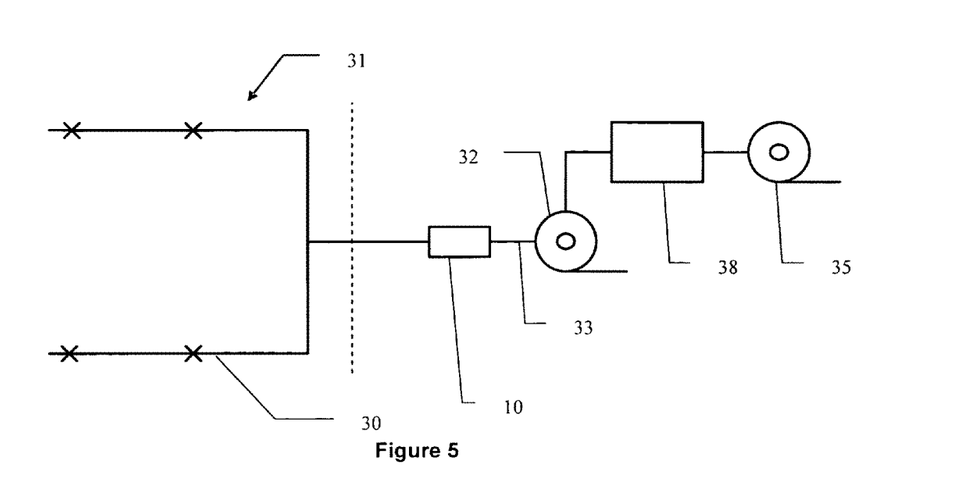
FIG. 5 is a schematic view of a first example of a smoke detector system including the smoke attenuator of FIG. 1.
Figure 6:
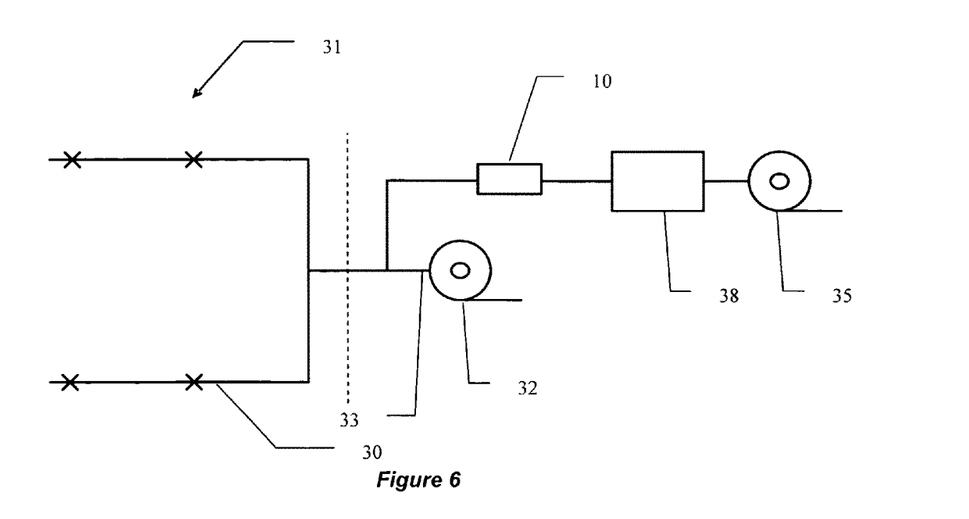
FIG. 6 is a schematic view of a second example of a smoke detector system including the smoke detector of FIG. 1.

Theoretical airflows are shown for illustrative purposes in FIG. 1. In this example, the sub-flow passing through the nine apertures in the outer ring of the plate 21 pass through the filter 20, which removes substantially all particulate matter, be it smoke or dust. The sub-flow passing through the single aperture 23 in the centre of the plate does not pass through the filter, and therefore retains substantially all particles from the sample entrained in the air flow.

In the present case the filter has low impedance compared to the flow resistance caused by the apertures 22 and 23. As the filter clogs, it will eventually increase the flow resistance to the air, decreasing the air flow through the filter and thereby increasing the proportion of the air that passes through the attenuator 10 without being filtered.

If the impedance of the attenuator is dominated by the flow restriction caused by the apertures, the ratio of filtered air to non-filtered air can be made to change more slowly, effectively increasing the life of the filter. If the restriction caused by the apertures is much greater than that of the filter, the dilution ration can be kept substantially constant over the effective life of the filter.

In a particularly preferred embodiment, the plurality of apertures 22 and 23 in the flow splitter 18 are all the same size. Thus all of the apertures will tend clog at approximately the same rate, meaning that over time as the apertures become constricted due to the build up of contaminants, the balance of flow between the unfiltered and filtered sub-flows will remain substantially constant.

Once the filter 20 clogs to a significant extent, it is possible to measure airflow changes either overall or specifically of the filtered air flow, to ascertain whether it is necessary to change the filter.

Another aspect of the present design is that as when the filter clogs to an extent that results in a change in the proportion of air flowing through the filter compared to air that bypasses the filter, the effective smoke levels reaching the detector increase, meaning that if a filter is left in the system of the present invention too long it will cause an increase in the smoke detected, thus failing in a safe manner. This increase will be gradual as the system clogs, and may therefore be determined by software that checks the smoke levels over an extended period of time to determine filter life.

Another method of determining filter life is to measure the airflow of the filtered air and to compare it to the airflow bypassing the filter. This ratio will give a smoke dilution factor that will allow the smoke detection system to apply a correction factor to determine true smoke levels in a sample. If the filter clogs over time, affecting flow rates through the filter, the air flow meters will determine the new correction factor to be applied to the output of the detection chamber. In some embodiments it would also be possible to measure filter life by determining when the airflow through the filter had dropped to a predetermined level.

As noted above a feature of a preferred embodiment of the present invention is that all apertures in the flow splitter 18 are the same size. One benefit of this arrangement is that airflow through the apertures can cause material to settle around the aperture periphery. Over time this will eventually reduce airflow significantly. Aspirated smoke detectors have a requirement that they pass sampled air at a sufficient rate to the detector so that smoke levels can be determined quickly, for example so that sampled air containing smoke levels above the preset level will trigger an alarm within one minute of the air being sampled. As the apertures become smaller, the airflow for a given aspirator will drop, and eventually the time delay will exceed the specifications. Aspirators are somewhat restricted in size and power due to packaging constraints within the smoke detector system, and power constraints. For this reason aspirators are commonly fitted with flow sensors to determine whether the flow is above a predetermined level.

In the present example the apertures are 3.5 mm in diameter, which provides sufficient airflow through the smoke attenuator, and also provides sufficient impedance over the impedance caused by the filter.

While the present example shows a flow splitter 18 having one aperture 23 for unfiltered air and 9 apertures 22 for filtered air, there may be any number of apertures for filtered and unfiltered air flows provided the ratio of apertures for the filtered sub-flow and the unfiltered sub-flow are known. This ratio should be provided to the detector so that it can ascertain the dilution factor to apply to the air sample entering the detector. For example, if the dilution factor is 10 (as in the example in FIG. 1) then if the detector is to alarm when smoke levels exceed an obscuration of 1% per meter, then the detector will need to alarm when the air outlet from the smoke attenuator exceeds 0.1% per meter. Aspirated smoke detectors such as the Vesda LaserPLUS manufactured and sold by Vision fire & Security Pty Ltd, can easily detect obscurations of 0.1% and lower.

As discussed above, the life of an aspirated smoke detector sampling air capable of causing a constant obscuration of 1% per meter, can be significantly lower than the life of an aspirated detector sampling air capable of causing an obscuration of at 0.1% per meter, due to failure modes such as blocking of detector flow paths, contamination of the sampling chamber causing an increasingly higher background level of light etc.

FIGS. 3 and 4 show one example of a filter element that can be used in an embodiment of the present invention. Such filter elements have a high surface area per volume and allow air to flow with low impedance. Filters may have a pore size, which is an aperture size that prevents particles larger than the pore passing through the filter, chosen to remove all particles above a given size, or be configured to effectively block all particulate material. In some filters, such as a foam filter, the effective pore size may be smaller than the measurable pore size as the particle may have to travel along a significant pathway to pass through the filter material.

In the present example, the filter material removes substantially all particles able to be measured by the detector. In practice there is no such device as a perfect filter, and given the physical constrains to the filter, it may be necessary to use a filter that merely removes some particles from the air, or is selectively lets through particles under a certain size.

It should be noted that in an alternative embodiment the flow splitting arrangement could be located after the filter. In this case, rather than splitting the flows prior to filtering, the flow splitting arrangement can operate by limiting the flow through the filter and through the unfiltered flow paths by restricting the amount of air flowing out of them.

Embodiments of the flow splitting arrangement described herein could also be used in other applications to divide a fluid flow into a plurality of sub-flows. Certain embodiments may be used in other applications where maintaining a balance between a plurality of sub-flows is desirable. Two exemplary smoke detection systems incorporating a smoke attenuator 10 according to an embodiment of the present invention are shown in FIGS. 5 and 6. The smoke detection system of FIGS. 5 and 6 each include a smoke detector 38 configured to detect smoke in an air sample taken from a monitored a region 31.

In FIG. 5 air from the region 31 is drawn to the detector 31 via a pipe network 30 by aspirator 32. All the air drawn from the region 31 passes through a smoke attenuator 10 made in accordance with an embodiment of the present invention. The attenuator 10 reduces the smoke level in the sample flow to, for example, one-tenth its original value. After leaving the smoke attenuator 10, part of the conditioned sample flow passes through the main pipe 33 to the aspirator 32 and is dumped to atmosphere. A second portion of the air sample is drawn along sample pipe 34 and through a detection chamber 38, such as a LaserPLUS chamber by a second aspirator 35.

FIG. 6 is similar to FIG. 5 except only the portion of the sample flow that enters the detection chamber 38 passes through the attenuator 10, with the portion of the air that is exhausted to atmosphere without undergoing analysis remaining unfiltered.

The smoke attenuator 10 may also be used with a known smoke detector such as a VESDA air sampling smoke detector, produced by Vision Fire & Security Pty Ltd, which operates with a single aspirator across the detection chamber. It is not important from a detection perspective whether the smoke attenuator is placed in the full flow of the air through the main pipe, or if the smoke attenuator only filters the air in the sample pipe, The smoke attenuator can also be used in full flow systems where all of the air drawn through the main pipe passes through a detection chamber.

In another example (not shown) there may be an aspirator in each flow path to assist or cause flow through the flow paths. An aspirator may be located in a filtered flow path, and another aspirator in an unfiltered flow path. A flow sensor may be in each flow path as well, so that a controller can determine the flow ratios in each flow path, and therefore ascertain the ratio of filtered air to unfiltered air. This arrangement would allow flow rates through the flow paths to be monitored and adjusted to produce a desired outcome. One desired outcome may be to keep the ratio of filtered air to unfiltered at a constant level.

The air sampled in the flow paths may be the full flow through sampling pipes, or may be a sub-sample of the air through the sampling pipes. Typically a sub-sample is used where a main aspirator draw air through the sampling pipes, which can be adjusted to produce an appropriate air transit time. Aspirated smoke detectors are required to alarm within a certain elapsed time of the smoke being drawn into the sampling point. It is therefore necessary to maintain a sufficient flow rate through the sampling pipes to attain the transport time necessary to detect smoke within the time limits. If variable speed aspirators are used in the flow paths of the smoke attenuator, then it may be necessary to use a sub-sample arrangement.

In the above example, it is possible to use a controller to vary the rate of flow in each flow path to achieve a particular smoke level at the detector. For example, if background particles levels are at 1% per meter obscuration, and the detector is able to accurately measure smoke levels lower than 0.1%, then by detecting the smoke levels in the air, it is possible to vary the flow rate through each flow path to reduce the smoke level in the detector to the predetermined level. This has the advantage that the life of the detector can be prolonged due to the reduced level of smoke in the detector flow paths, reducing contamination of the detection chamber, apertures etc. In order to determine if a threshold smoke level has been breached, the detector monitors the smoke level in the detection chamber, and the flow rates in each flow path, and can then determine the actual level of smoke in the sampling pipes.

As an example of the benefit of the smoke attenuator of the type described herein, if 80% of the inlet flow passes through a “Total Filter” (also known as a HEPA filter) while 20% remains unfiltered then the concentration of smoke will fall to one-fifth of the original. Consequently, the life expectancy of the detection chamber or the detector itself may be increased fivefold over a detector that does not have any filter, if clogging or background noise levels in the chamber are a failure mode. Of course, the fire alarm threshold(s) applied must also be adjusted to one-fifth of their ‘usual’ setting—but this is not a problem in polluted environments, since the thresholds are normally at the upper range of the detector’s sensitivity. As such, while the smoke attenuator described herein is useful in many environments, it is particularly useful in environments having high background smoke or dust levels, and for use with sensitive detectors.

As can be seen from the above, the filter arrangement of the preferred embodiment operates by dividing an airflow into a number of sub-flows. In the illustrative embodiments described herein the airflow is split into two sub-flows, but it may be more. One or more of the sample flows are filtered and the flows are re-combined to produce a conditioned flow. The flow rate (preferably relative flow-rate) of each sub-flows is controlled to control the relative proportion of the airflow entering each sub-flow. This will typically be performed by restricting the passage of each sub-flow, either before or after filtering. The resulting conditioned flow can then be used downstream, e.g. by being provided to a particle detector for analysis.

Whilst the exemplary devices for implementing this method that have been described herein as a discrete filter arrangement in a housing, the present invention should not be considered as being limited to this form. Alternatively, an embodiment may be implemented in using a network or pipes or ducts, to separate the fluid flows, wherein the content of some, but not all pipes is filtered before recombination. In this case the flow balance between the paths can be performed controlling the flow in each pipe or duct at any point between and including, the point of division of the flows and the point of recombination of flows.

The reference to any prior art in this specification is not, and should not be taken as, an acknowledgment or any form of suggestion that that prior art forms part of the common general knowledge in Australia.

Throughout this specification, unless the context requires otherwise, the word “comprise”, or variations such as “comprises" or "comprising", will be understood to imply the inclusion of a stated step or integer or group of steps or integers but not the exclusion of any other step or integer or group of steps or integers.

The claims defining the invention:

1. An apparatus in an airflow path before a particle detector, wherein the apparatus removes a substantially constant proportion of all sizes of airborne particles from the airflow over time, the apparatus further including a flow splitting arrangement for dividing the airflow into at least a first sub-flow and a second sub-flow, and a filtering arrangement for filtering the first sub-flow; and wherein the flow splitting device has an impedance to the passage of the sub-flows that is substantially greater than the flow impedance caused by the filtering arrangement.

2. The apparatus as claimed in claim 1, wherein the filtering arrangement removes substantially all particulate matter from the first sub-flow.

3. The apparatus as claimed in claim 2, wherein the filtering arrangement includes a HEPA filter.

4. The apparatus as claimed in claim 1 wherein the flow splitting arrangement includes a plurality of apertures through which the airflow passes to divide it into sub-flows.

5. The apparatus as claimed in claim 4 wherein the plurality of apertures formed in the flow splitting arrangement are substantially identical to each other.

6. The apparatus as claimed in claim 4 wherein the relative proportion of the airflow split into each sub-flow corresponds to the proportion of the apertures formed in the flow splitting arrangement configured to direct the airflow into each sub-flow.

7. The apparatus as claimed in claim 1 that further includes, at least one flow meter for determining a flow rate in any of the following:

an inlet to the apparatus;
an outlet from the apparatus;
a flow path through which one or more of the sub-flows passes.

8. The apparatus as claimed in claim 7, including a plurality of flow meters.

9. An arrangement for conditioning a fluid flow, the arrangement including:

a first flow path;
a second flow path,
a filter arrangement to filter the fluid flow in the first flow path; and
a flow splitting arrangement for splitting the fluid flow into either the first flow path or the second flow path,
wherein the impedance to the fluid flow caused by the flow splitting arrangement is greater than the impedance caused to the fluid flow by the filter.

10. An arrangement for conditioning a fluid flow including:

a chamber including a fluid inlet and a fluid outlet;
an unfiltered fluid flow path extending between the fluid inlet and the fluid outlet;
a filtered fluid flow path extending between the fluid inlet and the fluid outlet;
a filtering means for filtering the fluid flowing through the filtered fluid flow path;
a flow splitting arrangement for splitting the fluid flow into the filtered fluid flow path or the unfiltered fluid flow path,
wherein the impedance to the fluid flow caused by the flow splitting arrangement is greater than that caused by the filtering means.

11. The arrangement for conditioning a fluid flow as claimed in claim 10 in which the flow splitting arrangement includes at least one first aperture leading to the filtered fluid flow path and at least one second aperture leading to the unfiltered fluid flow path, and wherein the flow impedance caused by each first and second aperture is the substantially the same.

12. The arrangement for conditioning a fluid flow as claimed in claim 11 wherein the proportion of the fluid flow split into the filtered fluid flow path and unfiltered fluid flow path respectively is determined by the relative number of first and second apertures.

13. A method of filtering an air sample prior to introduction to a particle detection means, the method including:

dividing the air sample into at least two sample flows;
filtering one or more of the sample flows;
restricting the flow of the sample flows by an amount greater than a flow restriction caused by the filtering of the one or more sample flows; and
re-combining at least some of the sample flows prior to introduction to a particle detection means.

14. The method as claimed in claim 13 wherein the at least one sample flow is not filtered before being re-combined with another sample flow.

15. The method as claimed in claim 13 wherein step of restricting the one or more filtered sample flows is performed either before or after the filtering of the sample flow.

16. The method as claimed in claim 13, further including the step of measuring any one or more of;

a flow of filtered air;
a flow of unfiltered air;
a sample flow;
the flow of air prior to dividing it into sample flows; and
the flow of air after combining sample flows compared to a total flow.

* * * * *

UNITED STATES PATENT AND TRADEMARK OFFICE
CERTIFICATE OF CORRECTION

PATENT NO. : 8,118,918 B2
APPLICATION NO. : 12/224190
DATED : February 21, 2012
INVENTOR(S) : Ron Knox et al.

It is certified that error appears in the above-identified patent and that said Letters Patent is hereby corrected as shown below:

Title Pg, Item (57), under "Abstract", in column 2, line 7, after "arrangement" delete "10".

In column 2, line 18, delete "unfiltered" and insert -- un-filtered --, therefor.

In column 2, line 26, delete "unfiltered" and insert -- un-filtered --, therefor.

In column 3, line 22, delete "unfiltered" and insert -- un-filtered --, therefor.

In column 3, line 32, delete "unfiltered" and insert -- un-filtered --, therefor.

In column 3, line 47, delete "unfiltered" and insert -- un-filtered --, therefor.

In column 3, line 54, delete "unfiltered" and insert -- un-filtered --, therefor.

In column 3, line 60, delete "unfiltered" and insert -- un-filtered --, therefor.

In column 3, line 64, delete "unfiltered" and insert -- un-filtered --, therefor.

In column 4, line 29, delete "unfiltered" and insert -- un-filtered --, therefor.

In column 4, line 36, delete "unfiltered" and insert -- un-filtered --, therefor.

In column 4, line 38, delete "unfiltered" and insert -- un-filtered --, therefor.

In column 5, line 4, delete "unfiltered" and insert -- un-filtered --, therefor.

In column 5, line 7, after "distributor" insert -- 15 --.

In column 5, line 54, delete "unfiltered" and insert -- un-filtered --, therefor.

Signed and Sealed this
Seventeenth Day of April, 2012

David J. Kappos
*Director of the United States Patent and Trademark Office*

CERTIFICATE OF CORRECTION (continued)
U.S. Pat. No. 8,118,918 B2

In column 6, line 36, delete "unfiltered" and insert -- un-filtered --, therefor.

In column 6, line 38, delete "unfiltered" and insert -- un-filtered --, therefor.

In column 6, line 39, delete "unfiltered" and insert -- un-filtered --, therefor.

In column 7, line 11, delete "unfiltered" and insert -- un-filtered --, therefor.

In column 7, line 38, delete "unfiltered." and insert -- un-filtered. --, therefor.

In column 7, line 52, delete "unfiltered" and insert -- un-filtered --, therefor.

In column 7, line 55, delete "unfiltered" and insert -- un-filtered --, therefor.

In column 7, line 58, delete "unfiltered" and insert -- un-filtered --, therefor.

In column 8, line 25, delete "unfiltered" and insert -- un-filtered --, therefor.

In column 8, line 64, after "that" delete "that".

In column 10, line 3, in Claim 10, delete "unfiltered" and insert -- un-filtered --, therefor.

In column 10, line 10, in Claim 10, delete "unfiltered" and insert -- un-filtered --, therefor.

In column 10, line 19, in Claim 11, delete "unfiltered" and insert -- un-filtered --, therefor.

In column 10, line 24, in Claim 12, delete "unfiltered" and insert -- un-filtered --, therefor.

In column 10, line 45, in Claim 16, delete "unfiltered" and insert -- un-filtered --, therefor.